United States Patent [19]

Degner et al.

[11] Patent Number: 4,654,167

[45] Date of Patent: Mar. 31, 1987

[54] P-ALKOXYCYCLOHEXYLALKANOLS AND P-ALKOXYCYCLOHEXYLALKYL ESTERS AND THEIR USE AS SCENTS

[75] Inventors: Dieter Degner, Dannstadt-Schauernheim; Walter Gramlich, Edingen-Neckarhausen, both of Fed. Rep. of Germany; Werner Hoffmann, New York, N.Y.; Ludwig Schuster, Limburgerhof, Fed. Rep. of Germany

[73] Assignee: BASF Aktiengesellschaft, Ludwigshafen, Fed. Rep. of Germany

[21] Appl. No.: 794,795

[22] Filed: Nov. 4, 1985

[30] Foreign Application Priority Data

Nov. 8, 1984 [DE] Fed. Rep. of Germany ....... 3440825

[51] Int. Cl.[4] .................. C11B 9/00; C07C 43/18; C07C 43/196
[52] U.S. Cl. .................. 252/522 R; 568/664; 568/670; 560/231
[58] Field of Search ............ 568/664, 670; 560/231; 252/522 R

[56] References Cited

U.S. PATENT DOCUMENTS 4,181,631 1/1980 Shaffer et al. ................ 252/522 R

FOREIGN PATENT DOCUMENTS 2804075 12/1985 Fed. Rep. of Germany.
1294931 4/1962 France.

OTHER PUBLICATIONS

Nazarov et al., Chem. Abs., vol. 43 (1949) 2576–2577.
Journal of Chemical Society, 1980, pp. 762–763, Kametani et al., Studies on the Stereochemical Course of Selenium–Assisted Cyclisation: Biogenetic-Type Synthesis in the p-Menthan Series.
Dragaco-Report, vol. 11/12, 1981, pp. 39–46, Brunke, Sandelholz Riechstoffe.

*Primary Examiner*—Bernard Helfin
*Attorney, Agent, or Firm*—Oblon, Fisher, Spivak, McClelland & Maier

[57] ABSTRACT p-Alkoxycyclohexylalkanols and their esters of the general formula I

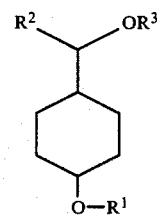

where $R^1$ is $C_1$–$C_7$-alkyl, in particular tert.-butyl, or is cyclohexyl, $R^2$ is $C_1$–$C_3$-alkyl, in particular methyl or ethyl, and $R^3$ is hydrogen, acetyl, propionyl or butyryl, and scent compositions containing these compounds I and processes for their preparation. The novel compounds have fine woody or sandalwood notes and can be used as scents and as components of scent compositions.

5 Claims, No Drawings

P-ALKOXYCYCLOHEXYLALKANOLS AND P-ALKOXYCYCLOHEXYLALKYL ESTERS AND THEIR USE AS SCENTS

The present invention relates to p-alkoxycyclohexylalkanols and their esters of the general formula

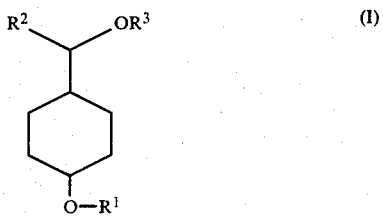

where $R^1$ is $C_1$-$C_7$-alkyl, in particular methyl or tert.-butyl, or cycloalkyl, $R^2$ is $C_1$-$C_3$-alkyl, in particular methyl or ethyl, and $R^3$ is hydrogen, acetyl, propionyl or butyryl, scent compositions containing these compounds I and processes for their preparation. The novel compounds constitute a class of novel woody scents. Furthermore, the novel compounds possess various types of smell extending over as wide a range as that implied by the term woody scent, from the earthy herbaceous type to the fine and expensive sandalwood type. Compounds in which $R^1$ is tert.-butyl have particularly fine sandalwood notes. They can be used as scents and as components of scent compositions.

The East Indian sandalwood oil is one of the well known natural substances which possesses extremely useful scent properties.

Natural sandalwood oil is obtained by steam distillation from heartwood and roots of sandalwood, which occurs in India and Malaysia. It is an important component of perfume mixtures having an oriental or exotic note.

Sandalwood is a specific plant which lives on the roots of other trees, long shoots emanating from its roots. It is cultivated from seed, and sandalwood oil can be obtained from it only after 25 to 30 years.

Accordingly, the sources in Asia have become rarer and there has been a shortage of this valuable oil over the past few years, which has led to an increase in the price of sandalwood oil.

The principal components of natural sandalwood oil are alpha-santalol and beta-santalol.

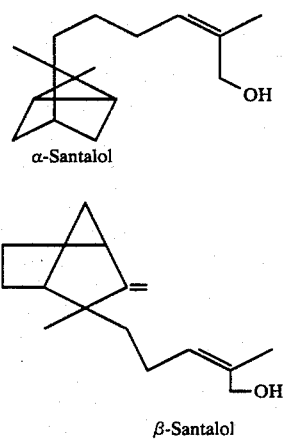

In spite of numerous attempts, no economical syntheses for alpha- and beta-santalol have been found; consequently, a large number of attempts have been made to replace the natural sandalwood oil with synthetic compounds having a sandalwood fragrance.

For example, the Dragoco Report, part 11/12 (1981), page 39, mentions compounds whith have a very large variety of structures and possess a sandalwood-like scent. The common feature of all these compounds is that they have relatively complicated structures and are obtainable only by very expensive methods.

It is an object of the present invention to find novel compounds which can be prepared industrially in a simple and cheap manner but nevertheless have a fine, strong woody fragrance, in particular a sandalwood fragrance, so that they can be used to replace natural sandalwood oil, even in demanding scent compositions.

We have found that this object is achieved, and that the p-alkoxycyclohexylalkanols and their esters of the general formula I possess interesting woody notes, and that the desirable note of the East Indian sandalwood oil is possessed especially by 1-(p-tert.-butoxycyclohexyl)-1-ethanol, in particular its cis-isomer.

It has been disclosed (loc. cit.) that 1-($\alpha$-hydroxyethyl)-4-(3-methylpent-3-yl)-cyclohexane of the formula III

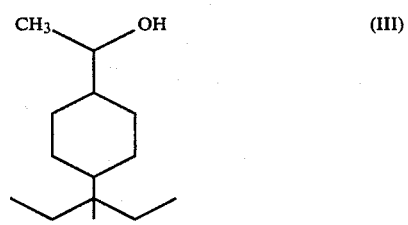

has a sandalwood-like scent; however, the said publication also states that even minor modification of this molecule results in a substantial weakening of the fragrance properties.

It was therefore surprising that the p-alkoxycyclohexylalkanols of the formula I, which are obtainable from industrially readily available and cheap intermediates, such as anisaldehyde or tert.-butoxybenzaldehyde, in technically simple steps and in good yields, possess a sandalwood fragrance which, particularly in the case of 1-(p-butoxycyclohexyl)-ethanol, bears a closer resemblance to that of the East Indian sandalwood oil than do the fragrances of the other synthetic products.

The novel fragrances can be prepared by various simple routes, in steps which are known per se and technically easy to carry out. For example, 1-(p-methoxycyclohexyl)-propan-1-ol is obtained in very good yields by reacting anisole with propionic anhydride in the presence of $ZnCl_2$ and then hydrogenating the resulting p-methoxypropiophenone. 1-(p-Tert.-butoxycyclohexyl)-ethan-1-ol is obtained by methylating 4-tert.-butoxybenzaldehyde by the Grignard method and then hydrogenating the product. 4-Tert.-butoxybenzaldehyde in turn has recently become obtainable industrially on a large scale, for example by electrochemical oxidation of tert.-butoxytoluene (cf. German Patent Application P No. 33 22 399.8 [U.S. Pat. No. 4,539,081]).

The present invention therefore relates to a process for the preparation of p-alkoxycyclohexylalkanols and their esters of the general formula I as claimed in claim 1, wherein a compound of the general formula IIa or IIb (IIa) (IIb)

where $R^1$, $R^2$ and $R^3$ have the meanings stated in claim 1 and in each case 3 or 2 non-neighboring dash lines are each an additional bond, or one or none of the dashed lines is an additional bond, is hydrogenated in a conventional manner, or a compound of the general formula IIc (IIc)

is reacted in a conventional manner with an organometallic compound which donates a radical $R^2$, and, if desired, the resulting alkanols alone are esterified.

Accordingly, the starting compounds used can be compounds of the general formula IIa or IIb which contain no double bonds, one double bond or two or three non-neighboring double bonds. The choice of suitable intermediates will be governed by economic considerations. The intermediates can be prepared in a variety of ways or are obtainable commercially as intermediates in many cases. The following scheme gives a brief and, understandably, incomplete overview of the possible methods for preparing the novel compound I:

For example, aromatic alkyl or cycloalkyl ethers can be converted by reaction route A, under Friedel-Crafts conditions, for example with carboxylic anhydrides or carboxylic acid chlorides and in the presence of a Lewis acid catalyst, to give the corresponding acylated aromatics, which can then be reduced to the compounds I in one or two stages.

In the two-stage process, known reagents, such as NaBH$_4$ or LiAlH$_4$ or a catalytic reduction e.g. with Raney nickel, can be employed in the first step. The subsequent step is preferably carried out using a rhodium or ruthenium catalyst. These catalysts hydrogenate the aromatic system without simultaneously cleaving the ether functions.

These ruthenium and rhodium catalysts are also useful for hydrogenating the oxyalkylated aromatics in one step to give the compounds I.

Catalysts which are generally used are from 0.5 to 10% strength by weight Ru or Rh catalysts on alumina or carbon carriers. However, the pure metals may also be used.

The conditions with respect to catalyst, solvent, reaction temperature, hydrogen pressure and reaction time can be varied within wide limits. In the single-stage process, the hydrogenation is preferably effected at from 25 to 200° C.

Examples of suitable solvents for the hydrogenation are alkanols, such as methanol or ethanol, ethers, such as tetrahydrofuran, hydrocarbons such as pentane, and acids, such as acetic acid; however, the hydrogenation may also be carried out in the absence of a solvent.

In synthesis route B, the corresponding aromatic aldehyde is reacted with a suitable organometallic reagent $R^2$-M, such as an alkyl Grignard compound. In this procedure, the aldehyde is preferably added dropwise to a solution of a metal-alkyl in an inert solvent and the resulting product then hydrolyzed, for example with an acid.

Preferably used organometallic compounds are Grignard reagents, such as alkyl-magnesium chloride, bromide or iodide, or lithium-alkyls, such as methyllithium.

In synthesis route C, oxyalkylated cyclohexenyl methyl ketones, which can be obtained, inter alia, by an ethynylation/rearrangement reaction sequence, are hydrogenated by a single-stage or two-stage method to give compounds of type I. In the more economical single-stage hydrogenation process, palladium, Raney nickel, cobalt, platinum, ruthenium and rhodium are generally used as hydrogenation catalysts. The reaction conditions for this single-stage process are not critical and may be varied within wide limits with respect to solvent, reaction temperature, hydrogen pressure and amount of catalyst. The preferred catalyst is Raney nickel, which is generally used in an amount of from 5 to 20% by weight, based on ketone. The temperature range is in general from 100 to 150° C., and the hydrogen pressure is from 5 to 100 bar. The novel alkoxycyclohexylalkanols of the formula I can be reacted with carooxylic anhydrides or carboxylic acid halides in a conventional manner to give the corresponding esters of the formula I (synthesis route D), which in turn possess other interesting woody notes. For example, reacting 1-(p-methoxycyclohexyl)-propan-1-ol with acetic anhydride gives the corresponding acetate, which has an interesting wild mushroom note.

It is also noteworthy that, for example, the 1-(p-tert.-butoxycyclohexyl)-ethan-1-ol obtained as a cis/trans mixture in the hydrogenation of 1-(p-tert.-butoxyphenyl)-ethan-1-ol can be separated into the cis and trans isomers by fractionation over a column containing 50 trays, and that the two isomers have different notes. While the cis product has a fine sandalwood note, the trans-isomer possesses a note which is similar to that of the West Indian cedarwood oil.

The novel compounds of the invention can be used as scents and therefore as components of scent compositions, such as perfumes and perfume bases, and for perfuming cosmetic and industrial products (soaps, detergents, etc.).

Very particularly important novel compounds are 1-(p-tert.-butoxycyclohexyl)-ethan-1-ol and 1-[4-(2-methyl-2-butoxy)-cyclohexyl]-ethan-1-ol, since both of these, in particular the first-mentioned compound, possess a sandalwood fragrance which is so fine and still so intense that they can be used as substitutes for natural sandalwood oil. They have the advantage of being much more stable than natural sandalwood oil. Moreover, they can be prepared easily and therefore substantially more economically and in virtually unlimited amounts. Although 1-(p-methoxycyclohexyl)-propan-1-ol has a somewhat weaker sandalwood note, it nevertheless possesses a very interesting fine woody note.

The structures of the novel compounds were confirmed by appropriate IR, $^1$H-NMR and mass spectra and by elemental analyses.

EXAMPLE 1

(a) Preparation of p-methoxyprpiophenone

A mixture of 108 g (1 mole) of anisole, 130 g (1 mole) of propionic anhydride and 7 g of anhydrous $ZnCl_2$ was refluxed for 5 hours, and the resulting propionic acid was then distilled over. After 50 g of distillate had been obtained, the mixture was cooled slightly and the residue was fractionated under 10 mbar. 103 g of p-methoxypropiophenone (bp. 150° C./10 mbar), bp. 273° C./1013 mbar) were obtained.

(b) Preparation of 1-(p-methoxycyclohexyl)-propan-1-ol

A mixture of 100 g of p-methoxypropiophenone, 250 ml of methanol and 5 g of a 5% strength ruthenium/active carbon catalyst was hydrogenated at 120° C. and under 150 bar until absorption of hydrogen was virtually complete. The catalyst was removed, the solvent was distilled off under 1013 mbar and the residue was then fractionated. 92 g of a colorless liquid having a boiling point of 73°-75° C. 0.01 mbar and a fine woody note were obtained.

EXAMPLE 2

Preparation of 1-(p-methoxycyclohexyl)-prop-1-yl acetate

A mixture of 161 g (0.93 mole) of 1-(p-methoxycyclohexyl)-propan-1-ol and 306 g (3 moles) of acetic anhydride was heated at 120°-140° C., and 260 g of an acetic anhydride/acetic acid mixture were distilled off in the course of 3 hours. The reaction mixture was cooled, 150 ml of diethyl ether were added, the mixture was neutralized with sodium carbonate and the solvent was then evaporated off. The resulting residue was then fractionated to give 189 g of a fraction which had a boiling point of 78° C./0.1 mbar and could be identified unambiguously as 1-(p-methoxycyclohexyl)-prop-1-yl acetate. The compound had an interesting wild mushroom fragrance.

EXAMPLE 3

(a) Preparation of 1-(p-tert.-butoxyphenyl)-ethan-1-ol 356 g (2 moles) of 4-tert.-butoxybenzaldehyde were added dropwise to 2 l of a 1.7 molar solution of methylmagnesium chloride (3.4 moles) in tetrahydrofuran at from 25 to 30° C. When the addition was complete, stirring was continued for a further 1.5 hours at 25° C., after which the product was carefully hydrolyzed with 100 ml of $H_2O$. Thereafter, a further 1.3 l of water and, finally, 0.4 l of a 37% strength sulfuric acid were added. Stirring was continued for 1 hour, after which the mixture was left to settle out, the two phases were separated, the lower aqueous phase was extracted with a further 400 ml of diethyl ether and the organic phases were combined and then washed with 100 ml of aqueous sodium bicarbonate solution and then with 100 ml of saturated sodium chloride solution.

The solvent was removed to give 380 g of a fraction which had a boiling point of 96–99° C./0.02 mbar and, on the basis of all analytical and spectroscopic data, could be identified as 1-(p-tert.-butoxyphenyl)-ethan-1-ol (yield 97.9%).

(b) Preparation of 1-(p-tert.-butoxycyclohexyl)-ethan-1-ol

In an autoclave, 200 g of 1-(p-tert.-butoxyphenyl)-ethan-1-ol in 500 g of dioxane and in the presence of 1 g of ruthenium hydroxide were flushed several times with nitrogen and hydrogen and then hydrogenated at 140° C. and under a hydrogen pressure of 300 bar until the pressure remained constant.

The catalyst and then the solvent were removed, after which the residue was distilled under 0.01 mbar to give 181 g of a colorless oil which boiled at 61° C./0.01 mbar and was shown by spectroscopic and analytical data to be an 80:20 cis/trans mixture of 1-(p-tert.-butoxycyclohexyl)-ethan-1-ol. The yield was 88% of theory.

The substance had a fine note similar to that of East Indian sandalwood oil.

Similar results are obtained if the washed organic phase obtained as described in Example 1a is hydrogenated directly.

(c) Separation of cis- and trans-1-(p-tert.-butoxycyclohexyl)-ethan-1-ol

A 75:25 mixture of cis- and trans-1-(p-tert.-butoxycyclohexyl)-ethan-1-ol obtained in the hydrogenation of 1-(p-tert.-butoxyphenyl)-ethan-1-ol was separated into the individual components by fractionation over a column containing 50 trays.

Distillation data:

(1) cis-1-(p-tert.-butoxycyclohexyl)-ethan-1-ol: bp. 72° C./0.01 mbar (2) trans-1-(p-tert.-butoxycyclohexyl)-ethan-1-ol: bp. 78° C./0.01 mbar.

While the cis product has a fine sandalwood note, the trans-isomer has a note similar to that of West Indian cedarwood oil.

EXAMPLE 4

Preparation of 1-(p-tert.-butoxycyclohexyl)-1-ethyl acetate

A mixture of 200 g (1 mole) of 1-(p-tert.-butoxycyclohexyl)-ethan-1-ol and 306 g (3 moles) of acetic anhydride was refluxed for 30 minutes. 260 g of a mixture of acetic acid and excess acetic anhydride were distilled off in the course of 3 hours under atmospheric pressure, and the residual acetic anhydride was then removed under reduced pressure (20 mbar). The residue was cooled to 20° C., washed with water and aqueous bicarbonate solution and again with water and then fractionated to give 218 g of a fraction which distilled over at 90° C./0.1 mbar and had an interesting herbaceous fruity note.

EXAMPLE OF USE

| Typical example of a perfume | parts by weight |
| --- | --- |
| 1-(p-tert.-butoxycyclohexyl)-ethan-1-ol | 350 |
| Vertofix ® (fixative from International Flavors and Fragrances) | 100 |
| p-tert.-butoxycyclohexyl acetate | 150 |
| γ-methylionone | 100 |
| linalyl acetate | 80 |
| linalool | 40 |
| benzyl acetate | 50 |
| cedrol | 10 |

| -continued | |
| --- | --- |
| Typical example of a perfume | parts by weight |
| dimethylbenzylcarbinyl acetate | 15 |
| alpha-hexylcinnamaldehyde | 20 |
| 2-heptylcyclopentanone | 10 |
| undecanal (20% strength in dipropylene glycol) | 2 |
| phenylethyl alcohol | 20 |
| limonene | 23 |
| hydroxycitronellal | 30 |
| | 1000 |

The fragrance effect of the composition which is achieved using the novel compound corresponds fairly exactly to that obtained by adding the same amount of East Indian sandalwood oil, instead of 350 parts by weight of 1-(p-tert.-butoxycyclohexyl)-ethan-1-ol, to the otherwise identical scent composition.

We claim:

1. A p-alkoxycyclohexylalkanol and its esters of the formula I

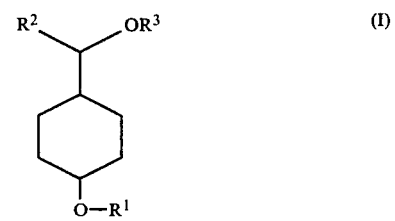

where $R^1$ is $C_1$-$C_7$-alkyl, $R^2$ is $C_1$-$C_3$-alkyl and $R^3$ is hydrogen, acetyl, propionyl or butyryl.

2. 1-(p-Tert.-butoxycyclohexyl)-ethan-1-ol.

3. A process for improving the fragrance of scent compositions, wherein a p-alkoxycyclohexylalkanol or one of its esters of the formula I

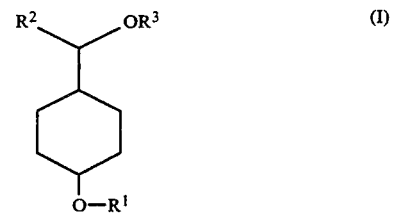

where $R^1$, $R^2$ and $R^3$ have the meanings stated in claim 1, is added to such a composition.

4. A scent composition containing an odor enhancing amount of a p-alkoxycyclohexylalkanol or one of its esters of the formula I

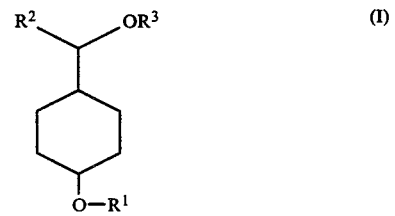

where $R^1$, $R^2$ and $R^3$ have the meanings stated in claim 1.

5. A scent containing an odor enhancing amount of 1-(p-tert.-butoxycyclohexyl)-ethan-1-ol.

* * * * *